Oct. 26, 1954 F. A. HENDERICKX Plant Pat. 1,311
TAXUS PLANT
Filed Dec. 10, 1953
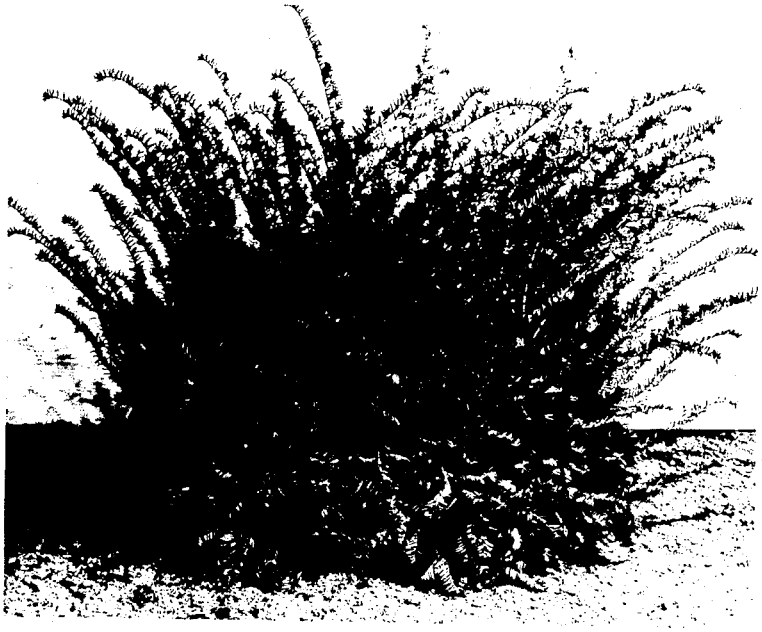
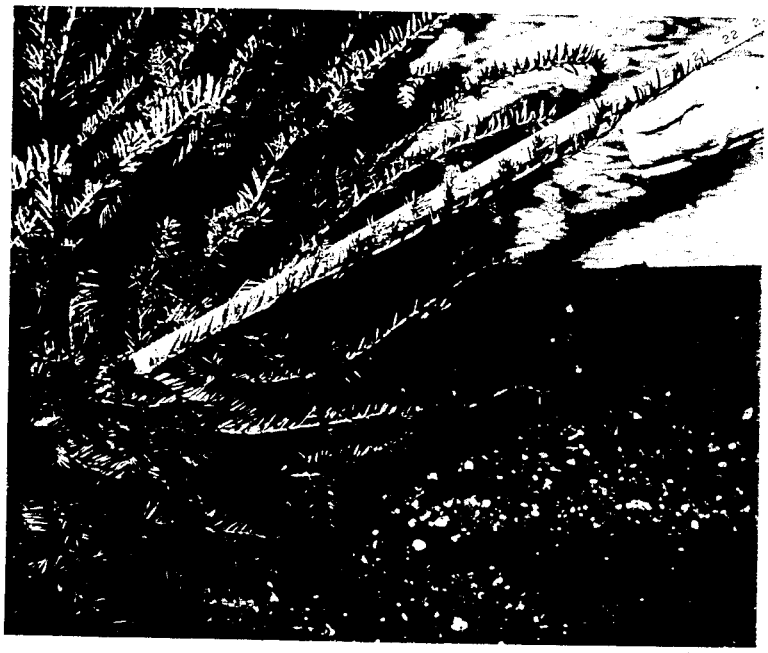
Inventor.
F. A. Henderickx
By: Robbins & Robbins
Attorneys.

Patented Oct. 26, 1954

Plant Pat. 1,311

UNITED STATES PATENT OFFICE 1,311

TAXUS PLANT

Fritz A. Henderickx, East Rutherford, N. J., assignor to Bobbink Nurseries, Inc., East Rutherford, N. J., a corporation of New Jersey Application December 10, 1953, Serial No. 397,498

1 Claim. (Cl. 47—59)

The present invention relates to a new and distinct variety of taxus plant (commonly known as yew), which was produced by me by crossing the unpatented varieties "Cuspidata" and "Cuspidata Densa."

The primary objective in making this cross was to produce a new ornamental type of taxus having a distinctly rapid habit of growth and a form of growth more pleasing to the eye than that of any other varieties of taxus plants now in commerce, while at the same time, maintaining hardiness as good as that of any other taxus variety now in commerce. This objective was fully achieved, since my new variety is particularly characterized by a rapidity of growth comparable to that of the variety "Cuspidata," and by a compactness, hardiness and attractive form comparable to that of "Cuspidata Densa."

In crossing the parent varieties above referred to, I obtained 146 seedlings, only one of which had the characteristics of exceptionally rapid growth, fine texture of foliage, compactness of growth and extreme hardiness. The latter plant was therefore selected to the exclusion of all of the other seedlings which were destroyed. Continued observation and asexual reproductions of the new variety were made by me, and it was definitely established that my new variety grows continuously from May to September under normal climatic conditions which prevail in the northeastern section of the United States. New growth from 18 to 21 inches is attained by my new variety each year, and I have found that my new variety is endowed with a definite and distinct commercial advantage of readily lending itself to propagation from summer cuttings as well as from winter cuttings.

As compared with the variety "Cuspidata," my new variety is a much more rapid grower, and the same size plant of my new variety can be produced in approximately one-half the growing time required for the variety "Cuspidata." Ordinarily, all varieties of taxus plants have two growing periods per year, the first occurring during late spring, and the second occurring in late summer. My new variety, however, grows continuously from May to September under normal climatic conditions, and may be propagated from both summer and winter cuttings due to this peculiar and distinct habit of growth, which enables portions of branches from 20 to 25 inches in length to be used in making three or more cuttings, all of which will root satisfactorily.

Asexual reproduction of my new variety by cuttings, as performed at East Rutherford, New Jersey, shows that the foregoing characteristics and distinctions come true to form and are established and transmitted through succeeding propagations.

The accompanying drawing shows a typical specimen plant of my new variety, and also an enlarged view of a portion of the plant, the latter view more clearly illustrating the foliage and branching habits of the plant.

The following is a detailed description of my new variety, with color terminology in accordance with Ridgway's Color Standards and Nomenclature:

Type: Hardy; spreading; outdoor seedling; ornamental evergreen; for use in ornamental garden plantings.

Class: Hybrid "Cuspidata."

Breeding: Seedling.

*Seed parent.*—"Cuspidata Densa."

*Pollen parent.*—"Cuspidata."

Propagation: Holds its distinguishing characteristics through succeeding propagations by cuttings.

Locality where grown and observed: East Rutherford, New Jersey.

Habit of growth: Primarily spreading; naturally compact, with graceful, somewhat weeping, branch ends; top center of plant somewhat taller than outer branches.

Branches: Sturdy; more than average number.

Foliage:

*Leaves.*—Narrower than "Cuspidata"; linear; 2-ranked; evergreen.

*Color.*—New growth: upper side—Forest Green, Plate XVII, 29, *m*; under side—Biscay Green, Plate XVII, 27, *i*. Old growth (1-year old): Upper side—Varley's Green, Plate XVIII, 31, *m*; under side—Rinnemann's Green, Plate XVIII, 31, *i*.

Stem: Color—new growth—total surface from Courge Green, Plate XVII, 25, *i* to Apple Green, Plate XVII, 29, –. Old growth (1-year old)—total surface from Aniline Black, Plate L, 69, *m* to Dusky Olive Green, Plate XLI, 25, *m*.

Trunk (4-year old growth): Color—total surface from Blackish Brown (1), Plate XLV, 1, *m* to Dusky Neutral Gray, Plate, –, *m*.

Flowers: Staminate; globose; 4 stamens each; dioecious. Color—Biscay Green, Plate XVII, 27, *i*.

Seeds: None.

Disease resistance: Highly resistant to all diseases to which taxus plants are generally subject, as determined by comparison with other varieties grow under comparable cultural conditions at East Rutherford, New Jersey.

I claim:

A new and distinct variety of taxus plant of the hybrid "Cuspidata" class, substantially as herein shown and described, characterized particularly as to novelty by its relatively rapid and vigorous habits of growth, by its extreme hardiness, by its generally spreading, compact and graceful form including its somewhat weeping branch ends and taller branches at the top center of the plant, by the relatively fine texture of its foliage, by its habit of growing continuously from May to September under normal climatic conditions prevailing in the northeastern section of the United States, and by its unique adaptability to asexual propagation in commercial quantities from both summer and winter cuttings.

No references cited.